US005643602A

United States Patent [19]

Ulmius

[11] Patent Number: 5,643,602
[45] Date of Patent: Jul. 1, 1997

[54] ORAL COMPOSITION FOR THE TREATMENT OF INFLAMMATORY BOWEL DISEASE

[75] Inventor: Jan Ulmius, Lund, Sweden

[73] Assignee: Astra Aktiebolag, Sodertalje, Sweden

[21] Appl. No.: 240,078

[22] Filed: May 9, 1994

Related U.S. Application Data

[63] Continuation of Ser. No. 855,623, filed as PCT/SE90/00738, Nov. 15, 1990, abandoned.

[30] Foreign Application Priority Data

Nov. 22, 1989 [SE] Sweden ................... 8903914

[51] Int. Cl.$^6$ ............... A61K 9/58; A61K 9/62; A61K 9/14; A61K 47/32
[52] U.S. Cl. ............. 424/462; 424/461; 424/494; 424/495; 424/497; 514/951; 514/925
[58] Field of Search ............... 424/451, 461–62, 424/494–95, 497, 471–72; 514/915, 925–26

[56] References Cited

U.S. PATENT DOCUMENTS

| | | | |
|---|---|---|---|
| 3,983,233 | 9/1976 | Brattsand et al. | 424/241 |
| 3,996,356 | 12/1976 | Brattsand et al. | 424/241 |
| 4,606,940 | 8/1986 | Frank et al. | 424/494 |
| 4,708,867 | 11/1987 | Hsiao | 424/462 |
| 4,966,770 | 10/1990 | Giannini et al. | 424/470 |

FOREIGN PATENT DOCUMENTS

| | | |
|---|---|---|
| 0040590 | 5/1981 | European Pat. Off. . |
| 1480811 | 1/1985 | European Pat. Off. . |
| 0054010 | 2/1985 | European Pat. Off. . |
| 0143764 | 6/1985 | European Pat. Off. . |
| 0278174 | 8/1986 | European Pat. Off. . |
| 0232690 | 8/1987 | European Pat. Off. . |
| 0218174 | 12/1987 | European Pat. Off. . |
| WO8300435 | 2/1983 | WIPO . |
| 8603676 | 12/1985 | WIPO . |

OTHER PUBLICATIONS

Wolman et al., *Scand. J. Gastroenterology*, vol. 24, Suppl. 15, pp. 146–147 (1989).
Manufacturer's Info. (FMC Corporation) re: "Aquacoat" (ethyl–cellulose), 1987: Altering Drug Release Rates–Coating Methods.
Manufacturer's Info. re: "Eudragit" (Apr. 1989), Lehmann, et al., Practical Course in Lacquer Coating and Survey of Course (Apr. 1989) relating to the use of Eudragit, pp. 1–167.
Johansson et al., *Eur. J. Respir. Dis.*, vol. 63, Suppl. 122, pp. 74–84, 1982.
Manufacturer's Info. re: "Aquacoat" (ethylcellulose), pp. 17–36, 1985.
H. Bechgaard "Critical factors influencing gastrointestinal absorption—what is the role of pellets?" Acta Pharmaceutic Tech 28 (1982) 149.
Wolman "Use of Oral Budesonide in a Patient with Small Bowel Crohn's Diseae . . . " Scand. J. Gastroenterol. 24 (1989) pp. 146–147.
Danielsson et al. "A controlled randomized trial of Budesonide 20. Prednisolone Retention Enemas . . . " Scand. J. Gastroenterol. 22 (1987) pp. 987–992.
Levine et al. "Coating of Oral Beclomethasone Dipropionate Capsules with Cellulose Acetate Phthalate . . . " Gastroenterology 92 (1987) pp. 1037–1044.
Richards et al. "Absorption of Delayed Release A Prednisolone in Ulcrative Colitis and Crohn's Disease", J. Pharm. Pharmacol. 37 (1985), pp. 757–758.
Jewell "Corticosteroids for the Management of Ulcerative Colitis and Crohn's Disease" 18 (1989) pp. 21–34.
Jamstedt et al. "Effect of Bethmethasone Treatment on Iodothyronimes and Thyroid Hormone–binding Proteins During Controlled Nutrition", Acta Endocrinologica 103 (1983) pp. 188–191.
Malchow et al., "Therapie des Morbus Crohn" Deutsche Medizinische Wochenschrift 1090 (1984) pp. 1811–1816.
Andersson et al., "In Vitro Biotransformation of Glucocorticoids in Liver and Skin Homogenate Fraction from Man, Rat and Hairless Mouse". J. Steroid Biochem. 16 (1982) pp. 787–795.
Anders Gamstedt et al 1983 "Effect of betamethasone treatment . . . " Acta Endocrinology 103: 188–191.
A. Kresznai et al. 1986 "Decreased number of steroid receptors . . . " Haematologia 19: 299–301.
P. Thomas et al. 1985 "Absorption of delayed—release . . . " J. Pharmaceutical Pharmocology 37: 757.
Kumana et al. 1982 "Beclomethasone dipropionate enemas . . . " Lancet 1 pp. 579–583 (Dialog).

*Primary Examiner*—Edward J. Webman
*Attorney, Agent, or Firm*—White & Case

[57] ABSTRACT

An oral pharmaceutical composition is described for targeted slow release in the treatment of inflammatory bowel diseases. Also described are pharmaceutical compositions for peroral treatment targeted to different areas of the intestinal tract afflicted by ulcerative colitis and certain aspects of Crohn's disease.

26 Claims, No Drawings

ORAL COMPOSITION FOR THE TREATMENT OF INFLAMMATORY BOWEL DISEASE

This application is a continuation of application Ser. No. 07/855,623, filed as PCT/SE90/00738 Nov. 15, 1990 now abandoned.

FIELD OF THE INVENTION

The present invention relates to oral pharmaceutical compositions for use in the treatment of inflammatory bowel diseases and the use of certain glucocorticosteroids in the preparation of pharmaceutical compositions for the treatment by the oral route of certain inflammatory bowel diseases.

BACKGROUND OF THE INVENTION

Inflammatory bowel disease is the term generally applied to two diseases, namely ulcerative colitis and Crohn's disease.

Ulcerative colitis is a chronic inflammatory disease of unknown aetiology afflicting only the large bowel and, except when very severe, limited to the bowel mucosa. The course of the disease may be continuous or relapsing, mild or severe. It is curable by total colectomy which may be needed for acute severe disease or chronic unremitting disease. Most patients with ulcerative colitis are managed medically rather than surgically.

Crohn's disease is also a chronic inflammatory disease of unknown aetiology but, unlike ulcerative colitis, it can affect any part of the bowel. Although lesions may start superficially, the inflammatory process extends through the bowel wall to the draining lymph nodes. As with ulcerative colitis, the course of the disease may be continuous or relapsing, mild or severe but, unlike ulcerative colitis it is not curable by resection of the involved segment of bowel. Most patients with Crohn's disease come to surgery at some time, but subsequent relapse is common and continuous medical treatment is usual.

For treatment of acute attacks of ulcerative colitis, glucocorticosteroids such as prednisone or prednisolone acetate are almost invariably used and given by mouth for the average acute attack or relapse, or locally, by enema.

After remission has been achieved, sulphasalazine is the maintenance treatment of choice in treating ulcerative colitis. This drug, however, has a significant number of side effects chiefly due to absorption of the sulphapyridine moiety from the colon. Recently compounds which contain only 5-aminosalicylic acid have been developed; these are as effective as sulphasalazine and do not have the sulphapyridine side effects but do have side effects of their own, notably diarrhoea.

Glucocorticosteroids are, however, not used for maintenance of remission in ulcerative colitis; doses that do not produce unacceptable side effects are ineffective, and patients who need chronic high dose glucocorticosteroids for control of their disease almost invariably are treated by colectomy.

As with ulcerative colitis, glucocorticosteroids are the treatment of choice for severe active Crohn's disease, but ideally only to achieve remission, after which they should be stopped. However, all too frequently the disease does not satisfactorily remit, and glucocorticosteroids may be necessary to maintain control of symptoms. Sulphasalazine is also useful in less severe cases, particularly for disease involving the colon.

Very often in Crohn's disease, however, primary medical treatment of the disease process is ineffective, and only symptomatic treatment is of value i.e. analgesics for pain and opiates for diarrhoea. Most patients eventually require surgery.

DISCLOSURE OF THE INVENTION

Our studies indicate that the compositions according to the present invention may advantageously be used in the treatment of ulcerative colitis including idiopathic proctitis and certain aspects of Crohn's disease by the oral route.

In ulcerative colitis the compositions can be used for the treatment of both active and chronic continuous disease and as a relapse preventing treatment (i.e. maintenance therapy once remission has been achieved).

In Crohn's disease the compositions can be used for the treatment of Crohn's colitis in its active phase and as a relapse preventing therapy (i.e. maintenance therapy once remission has been achieved), and for the treatment of the small intestine as a relapse preventing treatment (i.e. maintenance therapy).

It has been found that the diseases defined above can be treated using the anti-inflammatory steroids (22RS)-16α,17α-butylidenedioxy-11β,21-dihydroxy-pregna-1,4-diene-3,20-dione [I], the 22R-epimer of [I], (22RS)-16α,17α-butylidenedioxy-9α-fluoro-11β,21-dihydroxy-pregna-1,4-diene-3,20-dione [II], the 22R-epimer of [II], (22RS)-16α17α-butylidenedioxy-6α,9α-difluoro-11β,21-dihydroxy-pregna-1,4-diene-3,20-dione [III], the 22R-epimer of [III], (22RS)-21-acetoxy-16α17α-butylidenedioxy-11β-hydroxy-pregna-1,4-diene-3,20-dione [IA], the 22R-epimer of [IA], (22RS)-21-acetoxy-16α,17α-butylidenedioxy-9α-fluoro-11β-hydroxy-pregna-1,4-diene-3,20-dione [IIA], the 22R-epimer of [IIA], (22RS)-21-acetoxy-16α,17α-butylidene-dioxy-6α,9α-difluoro-11β-hydroxy-1,4-diene-3,20-dione [IIIA], the 22R-epimer of [IIIA], (22RS)-16α,17α-butylidenedioxy-11β,21-dihydroxy-pregna-4-ene-3,20-dione [IV], the 22R-epimer of [IV], (22RS)-16α,17α-pentylidenedioxy-11β,21-dihydroxy-pregna-4-ene-3,20-dione [V], the 22R-epimer of [V], (22RS)-21-acetoxy-16α,17α-butylidenedioxy-11β, hydroxypregn-4-ene-3,20-dione [IVA], the 22R-epimer of [IVA], (22RS)-21-acetoxy-16α,17α-pentylidenedioxy-11β, hydroxypregn-4-ene-3,20-dione [VA], the 22R-epimer of [VA], methyl (20RS)-16α,17α-butylidenedioxy-11β-hydroxy-androsta-1,4-diene-3-one-17β-carboxylate [VI], the 20R-epimer of [VI], methyl (20RS)-16α,17α-butylidenedioxy-9α-fluoro-11β-hydroxy-androsta-1,4-diene-3-one-17β-carboxylate [VII], the 20R-epimer of [VII], methyl (20RS)-16α,17α-butylidenedioxy-6α,9α-difluoro-11β-hydroxy-androsta-1,4-diene-3-one-17β-carboxylate [VIII], the 20R-epimer of [VIII], methyl (22RS)-16α,17α-butylidenedioxy-6α,9α-difluoro-11β-hydroxy-3,20-dioxopregna-1,4-diene-21-oate [IX] and the 22R-epimer of [IX].

Compound [I] has the approved name "budesonide".

Compound [I] and its 22R-epimer are particular preferred compounds.

Budesonide and compounds [II], [III], [IA], [IIA] and [IIIA] are described and claimed in Swedish Patent Specification 378 109. Budesonide is known to have an anti-inflammatory activity and, compared to prednisone, prednisolone and other glucocorticosteroids, an advantageous ratio between local and systemic effect when administered topically to the skin or to the lungs by inhalation.

Budesonide is a potent steroid, which is successfully used when locally treating (via aerosol) asthma and rhinitis. Also controlled trials of budesonide enema for locally treating proctitis and distal ulcerative colitis are in progress (Danielsson Å et al: A controlled randomized trial of budesonide versus prednisolone retention enemas in active distal ulcerative colitis, Scand. J. Gastroenterol. 22:987–992, 1987 and Danielsson Å et al: Controlled trial of budesonide enema and placebo in proctitis and distal ulcerative colitis. Scand. J. Gastroenterol. 24. supplement 159:88). The use of oral budesonide in the treatment of small bowel Crohn's disease in its active phase has been described (Wolman SL: Use of oral budesonide in a patient with small bowel Crohn's disease and previous pseudotumor cerebri secondary to steroids. Scand. J. Gastroenterol. 24, Supplement 158:146–147).

The characteristic profile of budesonide when used for the treatment of these diseases is a high anti-inflammatory effect at the place of application but a low degree of unwanted systemic glucocorticoid side effects. The low degree of systemic side effects of budesonide is a result of a high first pass liver metabolism transferring budesonide into substantially less active metabolites.

Especially the 22R-epimer of budesonide seems to be very promising in the treatment of inflammatory bowel diseases as hereinbefore defined when orally administered because, compared to budesonide it is more potent, is more rapidly metabolised by the liver and thus less available in the systemic circulation and thereby causing less unwanted systemic effects.

The 22R-epimers of compounds [I], [II], [III], [IA], [IIA] and [IIIA] are described and claimed in Swedish Patent Specification 378 110.

Compounds [IV], [V], [IVA], [VA] and the 22R-epimers thereof are described and claimed in European Patent Specification 54010.

Compounds [VI], [VII], [VIII] and the 20R-epimers thereof are described and claimed in European Patent Application 143 764.

Compound [IX] and the 22R-epimer thereof are described add claimed in European Patent Application 232 690.

We have surprisingly found that the above identified glucocorticosteroids administered by the convenient oral route are of great potential benefit in the treatment of inflammatory bowel diseases as hereinbefore defined.

The above mentioned compounds thus potentially represents a very significant advance over other glucocorticosteroids which exert their effects systemically and other drugs previously used for the management of Crohn's disease, particularly in avoiding the systemic side effects normally associated with glucocorticosteroid therapy. The high first pass liver metabolism of the drug renders possible its safe use in the maintenance therapy of the disease as well as achieving remission in the acute phase. Although Crohn's disease is not a very common condition, it is a chronic and often debilitating disorder that can benefit from a safer and more effective treatment.

In ulcerative colitis, the drug may help to reduce the number of patients having to undergo surgery and in addition, its lack of systemic effects makes it possible to use the drug for maintenance therapy once remission has been achieved.

The invention therefore provides pharmaceutical compositions comprising the glucocorticosteroids hereinbefore defined for use in the treatment by the oral route of bowel diseases as hereinbefore defined.

The invention also provides the use of the glucocorticosteroids as hereinbefore defined in the preparation of pharmaceutical compositions for the treatment by the oral route of bowel diseases as hereinbefore defined.

The invention further provides a method of treatment of bowel diseases as hereinbefore defined wherein an effective dose of a glucocorticosteroid as hereinbefore defined is administered by the oral route to a human or animal subject suffering from said bowel disease.

In order for the oral composition containing the glucocorticosteroids as hereinbefore defined to be applicable for the treatment of the bowel diseases as hereinbefore defined the composition must be adjusted to this particular purpose. The adjusted composition is a further aspect of the present invention, and it can be used generally when treating ulcerative colitis and Crohn's disease.

The transit time through the gastro-intestinal canal for different dosage forms are rather well known. When the dosage form has been emptied from the stomach the transit through the small intestine takes 3 to 5 hours. The residence time in the large intestine is considerably longer, 25 to 50 hours. Ideally, as long as the dosage form remains in the stomach no release should occur. If Crohn's disease in small intestine is going to be treated the release should continue during about 5 hours after the dosage form has left the stomach. If the large intestine is going to be treated the release should ideally start at caecum, and continue for up to 50 hours.

The present invention utilizes pharmaceutical formulation techniques to provide compositions of a glucocorticosteroid for treating the inflammatory diseases of the bowel as hereinbefore defined. The glucocorticosteroid must have a chance to reach the inflamed part of the bowel in sufficient concentration and for a sufficient long time to exert it's local action, in the case of Crohn's disease the whole bowel or only the small intestine and in the case of ulcerative colitis the caecum (cecum), colon and the rectum.

A multiple unit composition in a capsule has been found suitable for fulfilling the above-mentioned demands. In ulcerative colitis, the composition should be formulated so that the glucocorticosteroid is released preferentially during the passage of the colon. In Crohn's disease in the ileum the composition should be formulated so that the glucocorticosteroid is released preferentially during the passage of the small intestine. This can be accomplished by enteric and/or slow release coating of the units containing the glucocorticosteroid. Such formulations of glucocorticosteroids are novel.

The dosage range for treatment of the bowel diseases as hereinbefore defined is suitably 2–20 mg divided into 1 to 4 doses during a 24-hour period.

DETAILED DESCRIPTION

The units will have a size between 0.3 and 5 mm, preferably a size between 0.5 and 2 mm. The units will be administered in hard gelatine capsules, the size of which will depend on the dose administered.

Each unit comprises a core, a first layer on the core and a second layer on the first layer.

The core consists of a non-pareil seed, preferably having a diameter between 0.2 and 1.0 mm, to which the glucocorticosteroid is applied or a seed in which the glucocorticosteroid is homogeneously distributed. The excipients used to prepare the seeds comprise one or more of pharmaceutically acceptable materials, e.g. sugar, starch, microcrystalline cellulose, waxes and polymeric binding agents.

The first layer on the non-pareil seeds comprises the glucocorticosteroid and a water-soluble or water-insoluble polymer which acts both as binder for the glucocorticosteroid and as a rate-limiting layer for release of the glucocorticosteroid. Such polymers may be selected from cellulose derivatives, acrylic polymers and copolymers, vinyl polymers and other high molecular polymer derivatives or synthetic polymers such as methylcellulose, hydroxypropylcellulose, hydroxypropylmethylcellulose, ethylcellulose, cellulose acetate, polyvinyl pyrrolidone, polyvidone acetate, polyvinyl acetate, polymethacrylates and ethylene-vinyl acetate copolymer or a combination thereof. Preferred film-forming polymers are ethylcellulose or copolymers of acrylic and methacrylic acid esters (Eudragit NE, Eudragit RL, Eudragit RS) in aqueous dispersion form.

The first, optionally rate-limiting layer on the seeds with homogeneously distributed glucocorticosteroid comprises a water insoluble polymer or a mixture of water insoluble polymers or a mixture of water soluble and water insoluble polymers mentioned above.

The polymers in the second layer may be selected from the group of anionic carboxylic polymers suitable for pharmaceutical purposes and being soluble with difficulty at a low pH but being soluble at a higher pH, the pH limit for solubility being in the interval of pH 4 to pH 7.5, said group comprising cellulose acetate phthalate, cellulose acetate trimellitate, hydroxypropylmethylcellulose phthalate, polyvinyl acetate phthalate and acrylic acid polymers e.g. partly esterified methacrylic acid polymers such as Eudragit L, Eudragit L100-55 and Eudragit S. These polymers may be used alone or in combination with each other or in combination with water insoluble polymers mentioned before. Preferred polymers are the Eudragits in aqueous dispersion form. The anionic carboxylic polymer comprises 25 to 100 % of the total polymer content.

The coatings may optionally comprise other pharmaceutically acceptable materials which improve the properties of the film-forming polymers such as plasticizers, anti-adhesives, surfactants, and diffusion-accelerating or diffusion-retarding substances.

Suitable plasticizers comprise phthalic acid esters, triacetin, dibutylsebacate, monoglycerides, citric acid esters and polyethylene glycols. Preferred plasticizers are acetyltributyl citrate and triethyl citrate.

Suitable antiadhesives comprise talc and metal stearates.

The amount of the first coating applied on the units is normally in the range between 0.5% and 30% by weight, preferably between 1% and 15%. This amount includes in the relevant case the weight of the steroid as well. The amount of the second coating applied on the units is normally in the range between 1% and 50% by weight, preferably between 2% and 25%, calculated on the weight of the coated units. The remainder constitutes the weight of the seed.

The preparation of the controlled release pellet formulation according to the present invention is characterized in that a non-pareil seed is enclosed in a layer of a glucocorticosteroid as hereinbefore defined and a water soluble or water insoluble polymer or a seed with homogeneously distributed glucocorticosteroid as hereinbefore defined is optionally enclosed in a layer of a water insoluble polymer or a mixture of water insoluble polymers or a mixture of water soluble or water insoluble polymers which in turn is enclosed in a membrane of a film-forming anionic carboxylic polymer or a mixture of a film-forming anionic carboxylic polymer and a water insoluble polymer which permits release of the glucocorticosteroid as hereinbefore defined in a manner set out below.

The controlled release pellet formulation according to this invention is thus characterized in that the pellet comprises i) a core consisting of a non-pareil seed or a seed in which a glucocorticosteroid as defined below is homogeneously distributed and ii) in case of a core consisting of a non-pareil seed, a layer of a) a glucocorticosteroid selected from the group consisting of (22RS)-16α,17α-butylidenedioxy-11β,21-dihydroxypregna-1,4-diene-3,20-dione [I], the 22R-epimer of [I], (22RS)-16α,17α-butylidenedioxy-9α-fluoro-11β, 21-dihydroxy-pregna-1,4-diene-3,20-dione [II], the 22R-epimer of [II], (22RS)-16α,17α-butylidenedioxy-6α,9α-difluoro-11β,21-dihydroxy-pregna-1,4-diene-3,20-dione [III], the 22R-epimer of [III], (22RS)-21-acetoxy-16α,17α-butylidene-dioxy-11β-hydroxypregna-1,4-diene-3,20-dione [IA], the 22R-epimer of [IA], (22RS)-21-acetoxy-16α,17α-butylidene-dioxy-9α-fluoro-11β-hydroxy-pregna-1,4-diene-3,20-dione [IIA], the 22R-epimer of [IIA], (22RS)-21-acetoxy-16α,17α-butylidenedioxy-6α, 9α-difluoro-11β-hydroxy-1,4-diene-3,20-dione [IIIA], the 22R-epimer of [IIIA], (22RS)-16α,17α-butylidenedioxy-11β,21-dihydroxypregn-4-ene-3,20-dione [IV], the 22R-epimer of [IV], (22RS)-16α,17α-pentylidenedioxy-11β,21-dihydroxypregn-4-ene-3,20-dione [V], the 22R-epimer of [V], (22RS)-21-acetoxy-16α,17α-butylidene-dioxy-11β, hydroxypregn-4-ene-3,20-dione [IVA], the 22R-epimer of [IVA], (22RS)-21-acetoxy-16α,17α-pentylidene-dioxy-11β,hydroxypregn-4-ene-3,20-dione [VA], the 22R-epimer of [VA], methyl (20RS)-16α,17α-butylidenedioxy-11β-hydroxy-androsta-1,4-diene-3-one-17β-carboxylate [VI], the 20R-epimer of [VI], methyl (20RS)-16α,17α-butylidenedioxy-9α-fluoro-11β-hydroxy-androsta-1,4-diene-3-one-17β-carboxylate [VII], the 20R-epimer of [VII], methyl (20RS)-16α,17α-butylidenedioxy-6α,9α-difluoro-11β-hydroxy-androsta-1,4-diene-3-one-17β-carboxylate [VIII], the 22R-epimer of [VIII], methyl (22RS)-16α,17α-butylidenedioxy-6α,9α-difluoro-11β-hydroxy-3,20-dioxo-pregna-1,4-diene-21-oate [IX] and the 22R-epimer of [IX] and b) a pharmaceutical acceptable film forming water insoluble or water soluble polymer, or in case of a core consisting of a seed in which a glucocorticosteroid as defined above is homogeneously distributed, an optionally layer of a pharmaceutically acceptable film forming water insoluble polymer or a mixture of water insoluble polymers or a mixture of water soluble and water insoluble polymers and iii) a membrane surrounding said core and layer and containing a pharmaceutically acceptable film-forming anionic carboxylic polymer being soluble with difficulty at low pH but being soluble at a higher pH, either alone or in combination with a pharmaceutically acceptable film-forming water insoluble polymer, the thickness of said layer or said membrane and/or the ratio of said anionic carboxylic polymer to said insoluble polymer being effective to prevent release of said glucocorticosteroid from said pellet in gastric fluids, but to permit release of said glucocorticosteroid from said pellet in intestinal fluids at a rate allowing treatment of the part of the intestinal tract where the disease resides, i.e. at a rate corresponding to a release time of 1 to 50 hours, preferably 5 to 10 hours when treating the small intestine and 25 to 50 hours when treating the large intestine, said rate being measured in vitro as a dissolution rate of said unit in simulated gastric and intestinal fluids, when measured in a flow through cell at 8 mL/min and 37° C. substantially corresponds to the following for units intended for treating the small intestine:

a) not more than 10%, preferably not more than 5%, of the total glucocorticosteroid is released after two hours in simulated gastric fluid in said assembly, b) from 15 to 55%, preferably from 20 to 50%, of the total glucocorticosteroid is released after two hours in simulated intestinal fluid in said assembly, c) from 35 to 80%, preferably from 40 to 70%, of the total glucocorticosteroid is released after four hours in simulated intestinal fluid in said assembly, d) not less than 60, preferably 60 to 90%, of the total glucocorticosteroid is released after eight hours in simulated intestinal fluid in said assembly,.

e) not less than 80% of the total glucocorticoid steroid is released after twelve hours in simulated intestinal fluid in said assembly, and for units intended for treating the large intestine:

a) not more than 10%, preferably not more than 5%, of the total glucocorticosteroid is released after two hours in simulated gastric fluid in said assembly, b) from 5 to 30%, preferably from 10 to 30%, of the total glucocorticosteroid is released after four hours in simulated intestinal fluid in said assembly, c) from 20 to 65%, preferably from 35 to 55%, of the total glucocorticosteroid is released after twelve hours in simulated intestinal fluid in said assembly, d) from 40 to 95%, preferably from 55 to 85%, of the total glucocorticosteroid is released after twenty-four hours in simulated intestinal fluid in said assembly, e) not less than 70%, preferably not less than 80%, of the total glucocorticosteroid is released after forty-eight hours in simulated intestinal fluid in said assembly.

In one embodiment of the composition there is a layer which comprises budesonide or the 22R epimer thereof and a water soluble or water insoluble polymer beneath the membrane surrounding the pellet.

In another embodiment of the composition the polymeric material of the layer in which budesonide or its 22R epimer is embedded is selected from polyvinylpyrrolidone and hydroxypropylmethylcellulose or alternatively from ethylcellulose, cellulose acetate and copolymers of acrylic and methacrylic acid esters.

In still another embodiment of the composition the layer which comprises budesonide or its 22R epimer and a water soluble or water insoluble polymer includes one or more additional components selected from plasticizers, anti-adhesives adhesives and surfactants.

WORKING EXAMPLES

The following pharmaceutical compositions can be used in the treatment of bowel diseases according to the invention.

Example 1

|  | mg/capsule |
|---|---|
| Budesonide micronized | 1.0 |
| Sugar spheres | 321 |
| Aquacoat ECD 30 | 6.6 |
| Acetyltributyl citrate | 0.5 |
| Polysorbate 80 | 0.1 |
| Eudragit L100-55 | 17.5 |
| Triethylcitrate | 1.8 |
| Talc | 8.8 |
| Antifoam MMS | 0.01 |

Budesonide (32.2 g) was suspended in the Aquacoat ECD 30 dispersion (0.70 kg) with the aid of the Polysorbate 80 (0.42 g) together with acetyltributyl citrate (15.8 g). The mixture was sprayed on to sugar spheres (10.2 kg) in a fluid bed apparatus. The enteric coating consisting of the Eudragit L100-55 dispersion, (Eudragit L100-55 (0.558 kg), triethylcitrate (55.8 g), talc (0.279 kg), Antifoam MMS (0.44 g) and Polysorbate 80 (2.79 g)) was then sprayed on the spheres. The pellets were dried in the fluid bed apparatus, sieved and filled in hard gelatine capsules.

The finished pellets were then subjected to a dissolution test as follows:

Apparatus: Flow-through cells (Sotax Dissotest CE6, equipped with 12 mm cells) at a flow rate of 8 mL/min and at 37° C.

Medium: Simulated gastric fluid (SGF), pH 1.2 and simulated intestinal fluid (SIF), pH 7.5 according to USP without enzymes.

Method: For the dissolution test in simulated gastric fluid, 2.8 g of pellets, and for the test in simulated intestinal fluid, 1.4 g of pellets were placed in the cells and the test commenced. For specified time periods fractions were collected and analyzed for budesonide by a liquid chromatographic method. The percentage dissolution at each time point was calculated. The results are shown in Table 1.

TABLE 1

Dissolution of budesonide of Example 1

| Medium | Percentage dissolution after | | | | |
|---|---|---|---|---|---|
| | 1 hour | 2 hours | 4 hours | 8 hours | 12 hours |
| SGF | 1 | 2 | 3 | — | — |
| SIF | 34 | 53 | 75 | 92 | 97 |

Example 2

| | mg/capsule |
|---|---|
| Budesonide micronized | 2.0 |
| Sugar spheres | 292 |
| Auquacoat ECD 30 | 4.8 |
| Acetyltributyl citrate | 0.4 |
| Polysorbate 80 | 0.01 |
| Eudragit NE30D | 17.5 |
| Eudragit S100 | 17.5 |
| Talc | 17.5 |

Budesonide (3.5 g) was suspended in the Aquacoat ECD 30 dispersion (28.0 g) with the aid of the Polysorbate 80 (0.02 g) together with acetyltributyl citrate (0.63 g). The mixture was sprayed on to sugar spheres (510 g) in a fluid bed apparatus. The rate-limiting and enteric coating consisting of Eudragit S100 (30.0 g) and talc (30.0 g) suspended in the Eudragit NE30D dispersion (100 g) with the aid of Polysorbate 80 (0.3 g) was then sprayed on the spheres. The pellets were dried, sieved and filled in hard gelatine capsules.

The finished pellets were then subjected to a dissolution test as follows:

Apparatus: Flow-through cells (Sotax Dissotest CE6, equipped with 12 mm cells) at a flow rate of 8 mL/min and at 37° C.

Medium: Simulated gastric fluid (SGF), pH 1.2 and simulated intestinal fluid (SIF), pH 7.5 according to USP without enzymes.

Method: For the dissolution test in simulated gastric fluid and simulated intestinal fluid, 2.8 g of pellets were placed in the cells and the test commenced. For specified time periods fractions were collected and analyzed for budesonide by a liquid chromatographic method. The percentage dissolution at each time point was calculated. The results are shown in Table 2.

TABLE 2

Dissolution of budesonide of Example 2

| Medium | Percentage dissolution after (hours) | | | | | | | | |
|---|---|---|---|---|---|---|---|---|---|
| | 1 | 2 | 4 | 8 | 12 | 18 | 24 | 36 | 48 |
| SGF | 0 | 0 | 1 | — | — | — | — | — | — |
| SIF | 5 | 8 | 13 | 20 | 27 | 35 | 43 | 56 | 67 |

Example 3

| | mg/capsule |
|---|---|
| Budesonide micronized | 2.0 |
| Sugar spheres | 305 |
| Auquacoat ECD 30 | 5.0 |
| Acetyltributyl citrate | 0.4 |
| Polysorbate 80 | 0.14 |
| Eudragit NE30D | 12.6 |
| Eudragit S100 | 12.6 |
| Talc | 12.6 |

Budesonide (6.69 g) was suspended in the Aquacoat ECD 30 dispersion (56.0 g) with the aid of the Polysorbate 80 (0.04 g) together with acetyltributyl citrate (1.26 g). The mixture was sprayed on to sugar spheres (1020 g) in a fluid bed apparatus. The rate-limiting and enteric coating consisting of Eudragit S100 (42.0 g) and talc (42.0 g) suspended in the Eudragit NE30D dispersion (140 g) with the aid of Polysorbate 80 (0.42 g) was then sprayed on the spheres. The pellets were dried, sieved and filled in hard gelatine capsules.

The finished pellets were then subjected to a dissolution test as follows:

Apparatus: Flow-through cells (Sotax Dissotest CE6, equipped with 12 mm cells) at a flow rate of 8 mL/min and at 37° C.

Medium: Simulated gastric fluid (SGF), pH 1.2 and simulated intestinal fluid (SIF), pH 7.5 according to USP without enzymes.

Method: For the dissolution test in simulated gastric fluid, 2.8 g of pellets, and for the test in simulated intestinal fluid, 2.1 g of pellets were placed in the cells and the test commenced. For specified time periods fractions were collected and analyzed for budesonide by a liquid chromatographic method. The percentage dissolution at each time point was calculated. The results are shown in Table 3.

TABLE 3

Dissolution of budesonide of Example 3

| Medium | Percentage dissolution after (hours) | | | | | | | |
|---|---|---|---|---|---|---|---|---|
| | 1 | 2 | 4 | 8 | 12 | 18 | 24 | 48 |
| SGF | 0 | 1 | 1 | — | — | — | — | — |
| SIF | 6 | 10 | 17 | 27 | 35 | 46 | 55 | 80 |

Example 4

| | mg/capsule |
|---|---|
| Budesonide micronized | 0.5 |
| Sugar spheres | 286 |
| Auquacoat ECD 30 | 24.2 |
| Acetyltributyl citrate | 1.8 |
| Eudragit NE30D | 12.6 |
| Eudragit S100 | 12.6 |
| Talc | 12.6 |

Budesonide (0.90 g) was suspended in the Aquacoat ECD 30 dispersion (144 g) together with acetyltributyl citrate (1.82 g). The mixture was sprayed on to sugar spheres (510 g) in a fluid bed apparatus. The rate-limiting and enteric coating consisting of Eudragit S100 (22.5 g) and talc (22.5 g) suspended in the Eudragit NE30D dispersion (75.0 g) was then sprayed on the spheres. The pellets were dried, sieved and filled in hard gelatine capsules.

The finished pellets were then subjected to a dissolution test as follows:

Apparatus: Flow-through cells (Sotax Dissotest CE6, equipped with 12 mm cells) at a flow rate of 8 mL/min and at 37° C.

Medium: Simulated gastric fluid (SGF), pH 1.2 and simulated intestinal fluid (SIF), pH 7.5 according to USP without enzymes.

Method: For the dissolution test in simulated gastric fluid, 2.8 g of pellets, and for the test in simulated intestinal fluid, 2.1 g of pellets were placed in the cells and the test commenced. For specified time periods fractions were collected and analyzed for budesonide by a liquid chromatographic method. The percentage dissolution at each time point was calculated. The results are shown in Table 4.

TABLE 4

Dissolution of budesonide of Example 4

| Medium | Percentage dissolution after (hours) | | | | | |
|---|---|---|---|---|---|---|
| | 1 | 2 | 4 | 8 | 12 | 18 |
| SGF | 1 | 1 | 3 | — | — | — |
| SIF | 7 | 15 | 29 | 50 | 67 | 84 |

Absorption data for the budesonide formulation prepared in Example 1

Each of two healthy volunteers took the formulation in Example 1 corresponding to 9 mg of budesonide. Blood samples were drawn at different time-points up to 48 hours after drug administration. Plasma samples were analysed for budesonide by a specific HPLC-RIA method. The absorption process was estimated by the numerical point to point deconvolution method on plasma concentration data. The absorption values were scaled to the same final level by dividing the values with the absorption value at the last time-point when absorption was considered complete. The values are presented in Table 1A. The absolute bioavailability was 10.8% and 9.6% for the two subjects, respectively. For comparison, the absolute bioavailability of a fast releasing budesonide capsule is 10 to 15%, and the mean absorption time is less than 2 hours. Of the dose absorbed about 30% and 55% was absorbed in the time interval 2–12 hours in the two subjects, respectively. Absorption in this time interval probably occurs during the passage of the formulation through ileum, caecum and proximal colon.

TABLE 1A

Absorption of budesonide of Example 1

| Subj | Percentage absorption after (hours) | | | | | | |
|---|---|---|---|---|---|---|---|
| no. | 1 | 2 | 4 | 8 | 12 | 24 | 36 |
| 3 | — | 7 | 14 | 23 | 37 | 83 | 100 |
| 5 | 13 | 39 | 61 | 85 | 94 | 99 | 100 |

Absorption data for the budesonide formulation prepared in Example 2

Each of two healthy volunteers took the formulation in Example 2 corresponding to 20 mg of budesonide. Blood samples were drawn at different time-points up to 72 hours after drug administration. Plasma samples were analysed for budesonide by a specific HPLC-RIA method. The absorption process was estimated by the numerical point to point deconvolution method on plasma concentration data. The absorption values were scaled to the same final level by dividing the values with the absorption value at the last time-point when absorption was considered complete. The values are presented in Table 2A. The absolute bioavailability was 3.1% and 2.3% for the two subjects, respectively. For comparison, the absolute bioavailability of a fast releasing budesonide capsule is 10 to 15%, and the mean absorption time is less than 2 hours. Of the dose absorbed about 68% and 67% was absorbed in the time interval 6–36 hours in the two subjects, respectively. Absorption in this time interval probably occurs during the passage of the formulation through caecum and colon-rectum.

TABLE 2A

Absorption of budesonide of Example 2

| Subj | Percentage absorption after (hours) | | | | | | | | |
|---|---|---|---|---|---|---|---|---|---|
| no. | 2 | 4 | 6 | 8 | 12 | 24 | 36 | 48 | 60 | 72 |
| 4 | 5 | 15 | 24 | 29 | 48 | 80 | 92 | 96 | 98 | 100 |
| 5 | 5 | 19 | 33 | 43 | 57 | 87 | 100 | | | |

Absorption data for the budesonide formulation prepared in Example 3

Each of two healthy volunteers took the formulation in Example 3 corresponding to 20 mg of budesonide. Blood samples were drawn at different time-points up to 72 hours after drug administration. Plasma samples were analysed for budesonide by a specific HPLC-RIA method. The absorption process was estimated by the numerical point to point deconvolution method on plasma concentration data. The absorption values were scaled to the same final level by dividing the values with the absorption value at the last time-point when absorption was considered complete. The values are presented in Table 3A. The absolute bioavailability was 6.3% and 4.9% for the two subjects, respectively. For comparison, the absolute bioavailability of a fast releasing budesonide capsule is 10 to 15%, and the mean absorption time is less than 2 hours. Of the dose absorbed about 67% and 71% was absorbed in the time interval 6–36 hours in the two subjects, respectively. Absorption in this time interval probably occurs during the passage of the formulation through caecum and colon-rectum.

TABLE 3A

Absorption of budesonide of Example 3

| Subj | Percentage absorption after (hours) | | | | | | | | |
|---|---|---|---|---|---|---|---|---|---|
| no. | 2 | 4 | 6 | 8 | 12 | 24 | 36 | 48 | 60 | 72 |
| 1 | 6 | 16 | 27 | 35 | 53 | 83 | 94 | 98 | 99 | 100 |
| 3 | 1 | 2 | 6 | 16 | 28 | 57 | 78 | 91 | 97 | 100 |

Absorption data for the budesonide formulation prepared in Example 4

Each of two healthy volunteers took the formulation in Example 4 corresponding to 20 mg of budesonide. Blood samples were drawn at different time-points up to 72 hours after drug administration. Plasma samples were analysed for budesonide by a specific HPLC-RIA method. The absorption process was estimated by the numerical point to point deconvolution method on plasma concentration data. The absorption values were scaled to the same final level by dividing the values with the absorption value at the last time-point when absorption was considered complete. The values are presented in Table 4A. The absolute bioavailability was 16.2% and 3.4% for the two subjects, respectively. For comparison, the absolute bioavailability of a fast releasing budesonide capsule is 10 to 15%, and the mean absorption time is less than 2 hours. Of the dose absorbed about 71% and 44% was absorbed in the time interval 6–36 hours in the two subjects, respectively. Absorption in this time interval probably occurs during the passage of the formulation through caecum and colon-rectum.

TABLE 4A

Absorption of budesonide of Example 4

| Subj no. | Percentage absorption after (hours) | | | | | | | | |
|---|---|---|---|---|---|---|---|---|---|
| | 2 | 4 | 6 | 8 | 12 | 24 | 36 | 48 | 60 | 72 |
| 1 | 3 | 16 | 24 | 36 | 56 | 86 | 94 | 98 | 99 | 100 |
| 2 | 8 | 33 | 51 | 62 | 72 | 89 | 95 | 97 | 99 | 100 |

I claim:

1. A controlled release pellet formulation for oral administration in the treatment of inflammatory bowel diseases wherein the pellet, having a size between 0.3 mm and 5 mm diameter, comprises (i)
 a) a core consisting of a non-pareil seed or
 b) a seed in which a glucocorticosteroid as defined in this claim is homogeneously distributed; and (ii)
 a) in the case of the core consisting of a non-pareil seed, a layer surrounding said core of
  i)' a glucocorticosteroid selected from the group consisting of (22R,S)-16α,17α-butylidenedioxy-11β,21-dihydroxypregna-1,4-diene-3,20-dione (I); the 22R-epimer of (I); (22R,S)-16α,17α-butylidenedioxy-9α-fluoro-11β,21-dihydroxypregna-1,4-diene-3,20-dione (II); the 22R-epimer of (II); (22R,S)-16α,17α-butylidenedioxy-6α,9α-difluoro-11β,21-dihydroxy-pregna-1,4-diene-3,20-dione (III); the 22R-epimer of (III); (22R,S)-21-acetoxy-16α,17α-butylidenedioxy-11β-hydroxypregna-1,4-diene-3,20-dione (IA); the 22R-epimer of (IA); (22R, S)-21-acetoxy-16α-17α-butylidenedioxy-9α-fluoro-11β-hydroxypregna-1,4-diene-3,20-dione (IIA); the 22R-epimer of (IIA); (22R, S)-21-acetoxy-16α,17α-butylidenedioxy-6α,9α-difluoro-11β-hydroxypregna-1,4-diene-3,20-dione (IIIA); the 22R-epimer of (IIIA); (22R,S)-16α,17α-butylidenedioxy-11β,21-dihydroxypregna-4-ene-3,20-dione (IV); the 22R-epimer of (IV); (22R,S)-16α,17α-pentylidenedioxy-11β,21-dihydroxypregna-4-ene-3,20-dione (V); the 22R-epimer of (V); (22R, S)-21-acetoxy-16α,17α-butylidenedioxy-11β hydroxypregna-4-ene-3,20-dione (IVA); the 22R-epimer of (IVA); (22R,S)-21-acetoxy-16α,17α-pentylidenedioxy-11β hydroxypregna-4-ene-3,20-dione (VA); the 22R-epimer of (VA); methyl (20R,S)-16α,17α-butylidenedioxy-11β-hydroxy-androsta-1,4-diene-3-one-17β-carboxylate (VI); the 20R-epimer of (VI); methyl (20R, S)-16α,17α-butylidenedioxy-9α-fluoro-11β-hydroxy-androsta-1,4-diene-3-one-17β-carboxylate (VII); the 20R-epimer of (VII); methyl (20R,S)-16α,17α-butylidenedioxy-6α,9α-difluoro-11β-hydroxy-androsta-1,4-diene-3-one-17β-carboxylate (VIII); the 20R-epimer of (VIII); methyl (22R,S)-16α,17β-butylidenedioxy-6α,9α-difluoro-11β-hydroxy-3,20-dioxo-pregna-1,4-diene-21-oate (IX) and the 22R-epimer of (IX), and ii)' a pharmaceutically acceptable film-forming, water-insoluble or water-soluble polymer, the layer comprising about 0.5–30% of the pellet by weight, or b) in the case of the core consisting of a seed in which a glucocorticosteroid as defined in this claim is homogeneously distributed, a layer surrounding said core of a pharmaceutically acceptable, film-forming, water-insoluble polymer or a pharmaceutically acceptable mixture of film-forming, water-insoluble polymers, or a pharmaceutically acceptable mixture of film-forming, water-soluble and film-forming, water-insoluble polymers; and (iii) a membrane surrounding both said core and said surrounding layer and containing a pharmaceutically acceptable, film-forming, anionic carboxylic polymer being difficult to dissolve at a low pH but being soluble at a higher pH of about 4 to 7.5, the polymer being either alone or in combination with a pharmaceutically acceptable, film-forming, water-insoluble polymer, the membrane comprising about 1–50% of the pellet by weight, the thickness of said layer or said membrane, or the ratio of said anionic carboxylic polymer to said water-insoluble polymer being effective to prevent release of said glucocorticosteroid from said pellet in gastric fluids, but to permit release of said glucocorticosteroid from said pellet in intestinal fluids at a rate allowing treatment of the part of the intestinal tract where the disease resides, which rate corresponds to a release time in vivo of 1 to 50 hours.

2. A controlled release pellet formulation for oral administration in the treatment of inflammatory bowel diseases wherein the pellet, having a size between 0.3 mm and 5 mm diameter, comprises (i)
 a) a core consisting of a non-pareil seed or
 b) a seed in which a glucocorticosteroid as defined in this claim is homogeneously distributed; and (ii)
 a) in case of the core consisting of a non-pareil seed, a layer surrounding said core of
  i)' a glucocorticosteroid selected from the group consisting of (22R,S)-16α,17α-butylidenedioxy-11β,21-dihydroxypregna-1,4-diene-3,20-dione (I); the 22R-epimer of (I); (22R,S)-16α,17α-butylidenedioxy-9α-fluoro-11β,21-dihydroxypregna-4,1-diene-3,20-dione (II); the 22R-epimer of (II); (22R,S)-16α,17α-butylidenedioxy-6α,9α-difluoro-11β,21-dihydroxy-pregna-1,4-diene-3,20-dione (III); the 22R-epimer of (III); (22R, S)-21-acetoxy-16α,17α-butylidenedioxy-11β-hydroxypregna-1,4-diene-3,20-dione (IA); the 22R-epimer of (IA); (22R,S)-21-acetoxy-16α,17α-butylidenedioxy-9α-fluoro-11β-hydroxypregna-1,4-diene-3,20-dione (IIA); the 22R-epimer of (IIA); (22R,S)-21-acetoxy-16α,17α-butylidenedioxy-6α,9α-difluoro-11β- hydroxypregna-1,4-diene-3,20-dione (IIIA); the 22R-epimer of (IIIA); (22R,S)-16α,17α-butylidenedioxy-11β,21-dihydroxypregna-4-ene-3,20-dione (IV); the 22R-epimer of (IV); (22R, S)-16α,17α-pentylidenedioxy-11β,21-dihydroxypregna-4-ene-3,20-dione (V); the 22R-epimer of (V); (22R, S)-21-acetoxy-16α,17α-butylidenedioxy-11β hydroxypregna-4-ene-3,20-dione (IVA); the 22R-epimer of (IVA); (22R,S)-21-acetoxy-16α,17α-pentylidenedioxy-11βhydroxypregna-4-ene-3,20-dione (VA); the 22R-epimer of (VA); methyl (20R, S)-16α,17α-butylidenedioxy-11β-hydroxy-androsta-1,4-diene-3-one-17β-carboxylate (VI); the 20R-epimer of (VI); methyl (20R,S)-16α,17α-butylidenedioxy-9α-fluoro-11β-hydroxy-androsta-1,4-diene-3-one-17β-carboxylate (VII); the 20R-epimer of (VII); methyl (20R, S)-16α,17α-butylidenedioxy-6α,9α-difluoro-11β-hydroxy-androsta-1,4-diene-3-one-17β-carboxylate (VIII); the 20R-epimer of (VIII); methyl (22R,S)-16α,17α-butylidenedioxy-6α,9α-difluoro-11β-hydroxy-3,20-dioxo-pregna-1,4-diene-21-oate (IX) and the 22R-epimer of (IX), and ii) ' a pharmaceutically acceptable, film-forming, water-insoluble or water-soluble polymer, the layer comprising about 0.5–30% of the pellet by weight, or (b) in the case of the core consisting of a seed in which a glucocorticosteroid as defined in this claim is homogeneously distributed, a layer surrounding said core of a pharmaceutically acceptable, film-forming, water-insoluble polymer, or a pharmaceutically acceptable mixture of film-forming, water-insoluble polymers, or a pharmaceutically acceptable mixture of film-forming, water-soluble and film-forming, water-insoluble polymers; and (iii) a membrane surrounding both said core and said surrounding layer and containing a pharmaceutically acceptable, film-forming, anionic carboxylic polymer being difficult to dissolve at a low pH but being soluble at a higher pH of about 4 to 7.5 the polymer being either alone or in combination with a pharmaceutically acceptable, film-forming, water-insoluble polymer, the membrane comprising about 1–50% of the pellet by weight, the thickness of said layer or said membrane, or the ratio of said anionic carboxylic polymer to said water-insoluble polymer being effective to prevent release of said glucocorticosteroid from said pellet in gastric fluids, but to permit release of said glucocorticosteroid from said pellet in intestinal fluids at a rate allowing treatment of the part of the intestinal tract where the disease resides, which rate corresponds to a release time in vivo of 1 to 50 hours, said rate being measured in vitro as a dissolution rate of a dosage unit in simulated gastric and intestinal fluids, when measured in a flow-through cell at 8 ml/min and 37° C. and corresponds to a formulation for treating the small intestine wherein:

a) not more than 10% of the total glucocorticosteroid is released after two hours in simulated gastric fluid in said assembly, b) from 15 to 55% of the total glucocorticosteroid is released after two hours in simulated intestinal fluid in said assembly, c) from 35 to 80% of the total glucocorticosteroid is released after four hours in simulated intestinal fluid in said assembly, d) not less than 60% of the total glucocorticosteroid is released after eight hours in simulated intestinal fluid in said assembly, e) not less than 80% of the total glucocorticosteroid is released after twelve hours in simulated intestinal fluid in said assembly, and a formulation for treating the large intestine wherein:

f) not more than 10% of the total glucocorticosteroid is released after two hours in simulated gastric fluid in said assembly, g) from 5 to 30% of the total glucocorticosteroid is released after four hours in simulated intestinal fluid in said assembly, h) from 20 to 65% of the total glucocorticosteroid is released after twelve hours in simulated intestinal fluid in said assembly, i) from 40 to 95% of the total glucocorticosteroid is released after twenty-four hours in simulated intestinal fluid in said assembly, and j) not less than 70% of the total glucocorticosteroid is released after forty-eight hours in simulated intestinal fluid in said assembly.

3. A controlled release pellet formulation for oral administration in the treatment of inflammatory bowel diseases wherein the pellet, having a size between 0.3 mm and 5 mm in diameter, comprises (i)

a) a core consisting of a non-pareil seed or b) a seed in which a glucocorticosteroid is homogeneously distributed; and (ii)

a) in the case of the core consisting of a non-pareil seed, a layer surrounding said core of (i)' a glucocorticosteroid selected from the group consisting of (22R,S)-16α,17α-butylidenedioxy-11β,21-dihydroxypregna-1,4-diene-3,20-dione (I); the 22R-epimer of (I); (22R,S)-16α,17α-butylidenedioxy-9α-fluoro-11β,21-dihydroxypregna-1,4-diene-3,20-dione (II); the 22R-epimer of (II); (22R, S)-16α,17α-butylidenedioxy-6α, 9α-difluoro-11β,21-dihydroxy-pregna-1,4-diene-3,20-dione (III); the 22R-epimer of (III); (22R,S)-21-acetoxy-16α,17α-butylidenedioxy-11β-hydroxypregna-1,4-diene-3,20-dione (IA); the 22R-epimer of (IA); (22R,S)-21-acetoxy-16α-17α-butylidenedioxy-9α-fluoro-11β-hydroxypregna-1,4-diene-3,20-dione (IIA); the 22R-epimer of (IIA); (22R,S)-21-acetoxy-16α,17α-butylidenedioxy-6α,9α-difluoro-11β-hydroxypregna-1,4-diene-3,20-dione (IIIA); the 22R-epimer of (IIIA); (22R,S)-16α,17α-butylidenedioxy-11β,21-dihydroxypregna-4-ene-3,20-dione (IV); the 22R-epimer of (IV); (22R,S)-16α,17α-pentylidenedioxy-11β,21-dihydroxypregna-4-ene-3,20-dione (V); the 22R-epimer of (V); (22R, S)-21-acetoxy-16α,17α-butylidenedioxy-11β hydroxypregna-4-ene-3,20-dione (IVA); the 22R-epimer of (IVA); (22R, S)-21-acetoxy-16α,17α-pentylidenedioxy-11βhydroxypregna-4-ene-3,20-dione (VA); the 22R-epimer of (VA); methyl (20R, S)-16α,17α-butylidenedioxy-11β-hydroxy-androsta-1,4-diene-3-one-17β-carboxylate (VI); the 20R-epimer of (VI); methyl (20R, S)-16α,17α-butylidenedioxy-9α-fluoro-11β-hydroxy-androsta-1,4-diene-3-one-17β-carboxylate (VII);

the 20R-epimer of (VII); methyl (20R, S)-16α,17α-butylidenedioxy-6α,9α-difluoro-11β-hydroxy-androsta-1,4-diene-3-one-17β-carboxylate (VIII); the 20R-epimer of (VIII); methyl (22R,S)-16α,17α-butylidenedioxy-6α,9α-difluoro-11β-hydroxy-3,20-dioxo-pregna-1,4-diene-21-oate (IX) and the 22R-epimer of (IX), and (ii)' a pharmaceutical acceptable, film-forming, water-insoluble or water-soluble polymer, the layer comprising about 0.5–30% of the pellet by weight, or (b) in the case of the core consisting of a seed in which a glucocorticosteroid as defined in this claim is homogeneously distributed, a layer surrounding said core of a pharmaceutically acceptable, film-forming, water-insoluble polymer, or a pharmaceutically acceptable mixture of film-forming, water-insoluble polymers or a pharmaceutically acceptable mixture of film-forming, water-soluble and film-forming, water-insoluble polymers; and (iii) a membrane surrounding both said core and said surrounding layer and containing a pharmaceutically acceptable, film-forming, anionic carboxylic polymer being difficult to dissolve at a low pH but being soluble at a higher pH of about 4 to 7.5, either alone or in combination with a pharmaceutically acceptable, film-forming, water insoluble polymer, the thickness of said layer or said membrane or the ratio of said anionic carboxylic polymer to said water-insoluble polymer being effective to prevent release of said glucocorticosteroid from said pellet in gastric fluids, but to permit release of said glucocorticosteroid from said pellet in intestinal fluids at a rate allowing treatment of the part of the intestinal tract where the disease resides, which rate corresponds to a release time in vivo of 1 to 50 hours said rate being measured in vitro as a dissolution rate of a dosage unit in simulated gastric and intestinal fluids, when measured in a flow through cell at 8 mL/min and 37° C., and corresponds to the following formulation for treating the small intestine, wherein:

a) not more than 5% of the total glucocorticosteroid is released after two hours in simulated gastric fluid in said assembly, b) from 20 to 50% of the total glucocorticosteroid is released after two hours in simulated intestinal fluid in said assembly, c) from 40 to 70% of the total glucocorticosteroid is released after four hours in simulated intestinal fluid in said assembly, d) 60% to 90% of the total glucocorticosteroid is released after eight hours in simulated intestinal fluid in said assembly, e) not less than 80% of the total glucocorticosteroid is released after twelve hours in simulated intestinal fluid in said assembly, and a formulation for treating the large intestine, wherein f) not more than 5% of the total glucocorticosteroid is released after two hours in simulated gastric fluid in said assembly, g) from 10 to 30% of the total glucocorticosteroid is released after four hours in simulated intestinal fluid in said assembly, h) from 35 to 55% of the total glucocorticosteroid is released after twelve hours in simulated intestinal fluid in said assembly, i) from 55 to 85% of the total glucocorticosteroid is released after twenty-four hours in simulated intestinal fluid in said assembly, and j) not less than 80% of the total glucocorticosteroid is released after forty-eight hours in simulated intestinal fluid in said assembly.

4. The formulation according to claim 1 2 or 3 wherein the anionic carboxylic polymer ranges from 25% to 100% by weight of the total polymer content of said membrane.

5. The formulation according to claim 1, 2 or 3 wherein the anionic carboxylic polymer is selected from the group consisting of cellulose acetate phthalate, cellulose acetate trimellitate, polyvinyl acetate phthalate, hydroxypropylmethycellulose phthalate and methacrylic acid copolymer.

6. The formulation according to claim 1, 2 or 3 wherein the water insoluble polymer is selected from the group consisting of ethyl-cellulose, cellulose acetate, polyvinyl acetate, ethylene-vinyl acetate copolymer, amino methacrylate copolymers and polymethacrylic acid esters.

7. The formulation according to claim 1, 2 or 3 wherein the membrane includes one additional component selected from the group consisting of a plasticizer, an antiadhesive, a surfactant and a mixture thereof.

8. The formulation according to claim 1, 2 or 3 wherein the membrane ranges between 1 and 50% of the total weight of the pellet.

9. The formulation according to claim 1 2 or 3 wherein the glucocorticosteroid is budesonide or the 22R epimer thereof.

10. A formulation according to claim 1, 2 or 3, wherein the layer surrounding the core and beneath the membrane comprises budesonide or the 22R epimer thereof and a water-soluble or water insoluble film-forming polymer.

11. A formulation according to claim 10 wherein the layer includes one additional component selected from the group consisting of plasticizer, an antiadhesive, a surfactant and a mixture thereof.

12. The formulation according to claim 1, 2 or 3, wherein the layer beneath the membrane comprises a film-forming, water-insoluble polymer, a mixture of film-forming, water-insoluble polymers, or a mixture of water-insoluble and water-soluble, film-forming polymers.

13. A formulation according to claim 1, 2 or 3 wherein the polymeric material in which budesonide or the 22R epimer thereof is embedded is selected from the group consisting of polyvidone acetate, methylcellulose, hydroxypropyl cellulose, polyvinylpyrrolidone, hydroxypropylmethylcellulose, ethylcellulose, cellulose acetate, polyvinyl acetate, ethylene-vinylacetate copolymer, an amino methacrylate copolymer and a polymethacrylic acid ester.

14. A formulation according to claim 12 wherein the layer includes one additional component selected from the group consisting of a plasticizer, an antiadhesive, a surfactant and a mixture thereof.

15. The formulation according to claim 12 wherein the polymeric material is selected from the group consisting of polyvidone acetate, methylcellulonse, hydroxypropylcellulose, ethylcellulose, cellulose acetate, polyvinyl acetate, ethylene vinylacetate copolymer, an amino methacrylate copolymer and a polymethacrylic acid ester.

16. The formulation according to claim 1, 2 or 3 wherein said core comprises budesonide or the 22R epimer thereof homogeneously distributed in pharmaceutically acceptable excipients or budesonide or the 22R epimer thereof in a layer on a non-pareil seed wherein the seed has a diameter between 0.2 and 1.5 mm.

17. The formulation according to claim 1, 2 or 3 wherein the release time in vivo is 5 to 10 hours for treating the small intestine or 25 to 50 hours for treating the large intestine.

18. The formulation according to claim 2 wherein the in vitro dissolution rate of the dosage unit for treating the small intestine is not more than 5% of the total glucocorticosteroid released after two hours in the simulated gastric fluid; from 20% to 50% thereof released after two hours in the simulated intestinal fluid; from 40% to 70% thereof released after four hours in simulated intestinal fluid; from 60% to 90% thereof released after eight hours in simulated intestinal fluid and not less than 80% thereof released after twelve hours in simulated intestinal fluid.

19. The formulation according to claim 2 wherein the dissolution rate for a dosage unit intended for treating the large intestine is not more than 5% of the total glucocorticosteroid being released after two hours in simulated gastric fluid; from 10% to 30% thereof is released after four hours in simulated intestinal fluid; from 35% to 65 % thereof is released after twelve hours in simulated intestinal fluid; 55% to 85% thereof is released after twenty-four hours in simulated intestinal fluid; and not less than 80% thereof is released after forty-eight hours in simulated intestinal fluid.

20. The formulation of claim 1, 2 or 3 wherein the pellet is substantially free of precipitating electrolyte salts or cross-linking additives.

21. The formulation according to claim 1, 2 or 3, wherein the layer comprises between 1% and 15% (w/w) of the total weight of the coated pellet.

22. A pharmaceutical composition comprising the formulation according to claim 1, 2 or 3, useful for the treatment by the oral route of a bowel disease selected from the group consisting of ulcerative colitis, Crohn's colitis in its active phase, Crohn's colitis in its chronic phase as relapse-preventing therapy and Crohn's disease in the small intestines as a relapse preventing treatment.

23. A pharmaceutical composition as claimed in claim 22 wherein the bowel disease is ulcerative colitis.

24. The pharmaceutical composition as claimed in claim 22 wherein the glucocorticosteroid is budesonide or the 22R epimer thereof.

25. A capsule comprising a formulation of pellets according to claim 1, 2 or 3.

26. A process for the production of a pellet formulation according to any one of claims 1, 2 or 3 which comprises a) making a core of pharmaceutically acceptable excipients with the glucocorticosteroid homogeneously distributed therein and optionally enclosing the core with a water-insoluble polymer, or a mixture of water-insoluble polymers or a mixture of water-soluble and water-insoluble polymers, or b) enclosing a core of a non-pareil seed in a layer of a glucocorticosteroid and a water-soluble or water-insoluble polymer, and thereafter enclosing the coated core with a membrane of a film-forming, anionic carboxylic polymer, or a mixture of a film-forming, anionic carboxylic polymer and a water-insoluble polymer which permits release of the glucocorticosteroid in a manner set out in claim 1, 2 or 3.

* * * * *

UNITED STATES PATENT AND TRADEMARK OFFICE
CERTIFICATE OF CORRECTION

PATENT NO. : 5,643,602
DATED : July 1, 1997
INVENTOR(S) : Ulmius

It is certified that error appears in the above-indentified patent and that said Letters Patent is hereby corrected as shown below:

Claim 1 at column 14, line 7: "16α,17β" should be "16α,17α".

Claim 2 at column 14, line 57: "pregna-4,1-diene-" should be "pregna-1,4-diene-".

Claim 4 at column 18, line 7: "12 or 3" should be "1, 2 or 3".

Claim 9 at column 18, line 27: "12 or 3" should be "1, 2 or 3".

Claim 11 at column 18, line 35: insert -- a -- before "plasticizer".

Claim 15 at column 18, line 57: "methylcellulonse" should be "methylcellulose".

Signed and Sealed this

First Day of June, 1999

Attest:

Attesting Officer

Q. TODD DICKINSON

Acting Commissioner of Patents and Trademarks

UNITED STATES PATENT AND TRADEMARK OFFICE
CERTIFICATE OF CORRECTION

PATENT NO.    : 5,643,602
DATED         : July 1, 1997
INVENTOR(S)   : Jan Ulmius It is certified that error appears in the above-identified patent and that said Letters Patent is hereby corrected as shown below:

Title page,
Item [73] Assignee, delete "Astra Aktiebolg", and insert therefor -- Aktiebolaget Draco --.

Signed and Sealed this

Ninth Day of October, 2001

Attest:

NICHOLAS P. GODICI
Attesting Officer    Acting Director of the United States Patent and Trademark Office